United States Patent
Schlatter et al.

(10) Patent No.: US 7,307,043 B2
(45) Date of Patent: Dec. 11, 2007

(54) AQUEOUS NEONICOTINOID COMPOSITIONS FOR SEED TREATMENT

(75) Inventors: Christian Schlatter, Greensboro, NC (US); Ravi Ramachandran, Guelph (CA)

(73) Assignee: Syngenta Crop Protection, Inc., Greensboro, NC (US)

( * ) Notice: Subject to any disclaimer, the term of this patent is extended or adjusted under 35 U.S.C. 154(b) by 35 days.

(21) Appl. No.: 10/919,626

(22) Filed: Aug. 17, 2004

(65) Prior Publication Data

US 2005/0215432 A1  Sep. 29, 2005

(51) Int. Cl.
  *A01N 25/30* (2006.01)
  *A01N 43/88* (2006.01)
  *A01N 43/78* (2006.01)
  *A01N 43/653* (2006.01)
  *A01N 43/08* (2006.01)

(52) U.S. Cl. ............ 504/100; 424/405; 514/365; 514/229.2; 514/383; 514/467; 514/256; 514/422; 514/452; 514/563

(58) Field of Classification Search ............. 504/100; 514/292.2, 341, 342, 357, 365, 229.2, 383, 514/467, 256, 422, 492, 563; 424/405

See application file for complete search history.

(56) References Cited

U.S. PATENT DOCUMENTS

| | | | |
|---|---|---|---|
| 4,161,397 A | 7/1979 | Bellet et al. | |
| 4,306,027 A | 12/1981 | Alexander et al. | |
| 4,755,468 A | 7/1988 | Jung et al. | |
| 5,599,583 A | 2/1997 | Lew et al. | |
| 5,684,025 A | 11/1997 | Tsao et al. | |
| 5,846,905 A | 12/1998 | Damo et al. | |
| 6,488,949 B2 * | 12/2002 | Shafer et al. ............. | 424/405 |
| 6,503,904 B2 | 1/2003 | Schneidersmann et al. | |
| 2003/0050194 A1 | 3/2003 | Hopkinson et al. | |

FOREIGN PATENT DOCUMENTS

| | | |
|---|---|---|
| EP | 0609099 | 8/1994 |
| EP | 0790000 | 8/1997 |
| EP | 1319336 | 6/2003 |
| WO | 9500019 | 1/1995 |
| WO | 9940784 | 8/1999 |
| WO | 0028825 | 5/2000 |

OTHER PUBLICATIONS

Doyle P et al: "New Generation Seed Treatment Products for Canola (*Brassica napus, B. campestris*) and Mustard (*Sinapis alba, Brassica juncea*)", British Crop Protection Council Monograph, British Crop Protection Council, London, GB, No. 76, 2001, pp. 173-180, XP009015867, ISSN: 0306-3941, abstract.

Jonitz A et al: "Seed Testing and the Effect of Insecticidal Active Ingredients on the Germination and Emergence of Hybrid Maize Seed", Pflanzenschutz Nachrichten Bayer, Bayer, Leverkussen, DE, vol. 56, No. 1, 2003, pp. 173-207, XP009057321, ISSN: 0340-1723, p. 188, column 1, paragraph 2 figures.

"Agrochemical-coated rought rice deeds for pest resistance-prepd by coating seeds with adhesive resin fluid contg pesticide and surfacant", DERWENT, 1996, XP002286597, abstract.

Maude, S J: "The effects of surfactant and water volume on the coverage of seed surface by a seed treatment formulation"; Brighton Crop Protection Conference Pests and Idseases, vol. 2, 2002, pp. 507-514, XP009034608, ISSN: 0955-1506, abstract.

\* cited by examiner

*Primary Examiner*—Edward J. Webman
(74) *Attorney, Agent, or Firm*—Jacqueline Haley

(57) ABSTRACT

An aqueous composition suitable for applying insecticides or acaricides to plant propagation materials comprising water, an insecticidally or acaricidally effective amount of at least one nitroimino- or nitroguanidino-compound in free form or in agrochemically useful salt form and a blend of the following components, by weight:
a) 2-10% of a surface-active agent comprising a1) at least one anionic surfactant;
b) 4-20% of at least one inorganic solid carrier; and
c) 3-25% of at least one antifreeze agent.

In one embodiment, the aqueous composition further comprises a fungicidally effective amount of at least one fungicidally active compound.

The inventive composition is storage stable, ready-to-apply (RTA), ecologically and toxicologically favorable and has good fungicidal efficacy.

13 Claims, No Drawings

AQUEOUS NEONICOTINOID COMPOSITIONS FOR SEED TREATMENT

TECHNICAL FIELD

The present invention relates to aqueous compositions, to the preparation of such compositions and to a method of using such compositions for controlling insects and/or representatives of the order Acarina. The aqueous compositions of the invention have particular application in the protection of plant propagation materials, such as seeds, against insects and/or representatives of the order Acarina.

BACKGROUND

The use of synthetic insecticides to control insect pests in crops is a universal practice. This practice has gained a high degree of commercial success because it has been shown that such control can increase crop yield. However, effective use of insecticides requires sound management in view of insect resistance and environmental and worker exposure concerns. One solution applied to this problem has been the provision of new, more highly active insecticides in order to reduce the need for older acutely toxic insecticides and to reduce environmental loading rates.

One new class of insecticides that is gaining significant recognition in the market place is the so-called "neonicotinoid" insecticides. Insecticides of this class include nitroimino- or nitroguanidino-compounds, for example, the compounds imidacloprid, acetamiprid, and thiamethoxam that are described in U.S. Pat. Nos. 4,742,060 and 5,304,566 and EP580553A2, respectively.

Direct treatment of plant propagation materials (such as seeds) with insecticides are target applications which address the need for a reduction of environmental and worker exposure and pest resistance buildup when applied alone or in conjunction with foliar or furrow insecticide applications.

Seed treatments are used on a large variety of crops to control a large variety of pests. Seed treatments are commonly used to ensure uniform stand establishment and reducing yield loss by protecting the seedling against soil-borne insects. Systemic seed treatments may provide an alternative to traditional broadcast sprays of foliar insecticides in some instances.

Insecticide seed treatments come in a variety of formulations: dry flowables (DF), liquid flowables (LF), true liquids (TL), emulsifiable concentrates (EC), dusts (D), wettable powders (WP), suspoemulsions (SE), water-dispersible granules (WG) and others. Some are registered for use only by commercial applicators using closed application systems, others are readily available for on-farm use as dusts, slurries, water-soluble bags, or liquid ready-to-apply formulations.

Commercial seed treatment is often desirable due to the specialized equipment required to properly apply treatments or to treat large volumes of seed. An important concern of the commercial treater is equipment performance to ensure the delivery of a proper amount of active ingredient to the seed. This has become especially important with more modern insecticides that require only very small amounts of material (down to 1 g active ingredient per hundred weight of seed).

Conveniently, many seed treatment materials also are available for on-farm use. These are known as hopper-box or planter-box treatments wherein liquid or dry formulations are applied to seed as it passes through an auger from the transport bin or truck to the planter boxes. These formulations are a very convenient way to apply seed treatment onto bulk seed right before planting. Conventional dry treatments generally are formulated with talc or graphite which adheres the treatment chemical to the seed. Conventional liquid hopper-box treatments generally are made available as a fast-drying formulations. In any case, good seed coverage is required for maximum benefit from any seed treatment formulation.

However, obtaining thorough seed coverage can be difficult when attempting to treat seed. For example, dry formulations can present unacceptable worker exposure to the insecticidal active ingredient. Certain liquid formulations can become inhomogeneous on storage, such that particle size or viscosity do not remain constant. Additional problems can arise such as unacceptable drying times, material build-up in the seed treater, low seed flowability, poor seed coverage and dust-off of the insecticide from the seed prior to planting. As a result, handling is rendered difficult and the biological efficacy of the seed treatment is reduced.

There is a need in the art for alternative new liquid insecticidal seed treatment compositions that are effective for use with both commercial and on-farm seed treatment equipment.

SUMMARY

It has now been found, surprisingly, that specific filled aqueous insecticidal compositions based on the combination of a surfactant, an inorganic carrier, an antifreeze agent and an insecticide of the neonicotinoid class are storage stable, have improved flowability and have good adherence to plant propagation material with low dust-off, and have excellent performance on cold or frozen seed. The aqueous compositions of the invention have particular application in the protection of plant propagation materials, such as seeds, against insects and/or representatives of the order Acarina, but also are advantageously combined with fungicidally active compounds to control phytopathogenic fungi.

The present invention thus provides an aqueous composition suitable for applying insecticides or acaricides to plant propagation materials comprising water, an insecticidally or acaricidally effective amount of at least one nitroimino- or nitroguanidino-compound in free form or in agrochemically useful salt form and a blend of the following components, by weight:

a) 2-10% of a surface-active agent comprising a1) at least one anionic surfactant;

b) 4-20% of at least one inorganic solid carrier; and c) 3-25% of at least one antifreeze agent.

In one embodiment, the aqueous composition further comprises a fungicidally effective amount of at least one fungicidally active compound.

The aqueous compositions are prepared by intimately mixing the components with water, optionally using a concentrated premix prepared by wet milling the solid components, until an evenly dispersed phase is achieved.

The invention also provides for plant propagation materials treated with the aqueous composition and for a method for reducing insect or acarinal infestation of plant propagation materials such as seeds and seedlings. The method comprises contacting the seeds with an aqueous insecticidal/acaricidal composition according to the invention described above.

DETAILED DESCRIPTION

The inventors have discovered that a specific combination of surfactants (a), carriers (b) and antifreeze agents (c) and a neonicotinoid insecticide when used together provide aqueous compositions that are storage stable and are suitable for use in normal seed treatment equipment, such as a slurry seed treater, direct treater, panogen treater or a mist-o-matic treater as well as on-farm hopper-box or planter-box treatments. Propagation materials treated with the aqueous compositions dry quickly, have good flowability, suitable coverage and have little or no dust-off.

Active Ingredients

The term insecticide or insecticidally when used herein in connection with neonicotinoid compounds is intended to include or refer to both insecticidally and acaricidally active compounds.

The term nitroimino- or nitroguanidino-compound as utilized herein is intended to cover insecticidally and/or acaricidally active compounds of the so-called neonicotinoid class. In one embodiment, suitable nitroimino- or nitroguanidino-compounds include at least one neonicotinoid compound of formula (I)

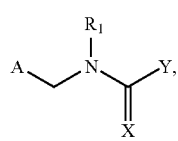

(I)

wherein

A is 2-chloropyrid-5-yl, 2-methylpyrid-5-yl, 1-oxido-3-pyridinio, 2-chloro-1-oxido-5-pyridino, 2,3-dichloro-1-oxido-5-pyridinio, tetrahydrofuran-3-yl, 5-methyl-tetrahydrofuran-3-yl or 2-chlorothiazol-5-yl group, Y is —N(R)(R$_2$), SR$_2$ or C$_1$-C$_4$-alkyl;

R is hydrogen, C$_1$-C$_6$alkyl, phenyl-C$_1$-C$_4$alkyl, C$_3$-C$_6$cycloalkyl, C$_2$-C$_6$alkenyl or C$_2$-C$_6$alkynyl;

R$_1$ and R$_2$ are independently of each other C$_1$-C$_4$-alkyl, C$_1$-C$_4$-alkenyl, C$_1$-C$_4$-alkinyl —C(=O)—CH$_3$ or benzyl; or together form a group —CH$_2$—CH$_2$—, —CH$_2$—CH$_2$—CH$_2$—, —CH$_2$—O—CH$_2$—, —CH$_2$—S—CH$_2$—, —CH$_2$—NH—CH$_2$— or —CH$_2$—N(CH$_3$)—CH$_2$—; and X is N—NO$_2$, N—CN or CH—NO$_2$; or, where appropriate, a tautomer thereof, in each case in free from or in salt form.

The compounds (I) may be in the form of tautomers. Accordingly, hereinbefore and hereinafter, where appropriate the compound (I) are to be understood to include corresponding tautomers, even if the latter are not specifically mentioned in each case.

The compounds of the formula (I) are capable of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, C$_1$-C$_4$alkanecarboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, C$_1$-C$_4$alkane- or aryl-sulfonic acids, for example methane- or p-toluene-sulfonic acid. Furthermore, compounds of formula (I) having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or tri-hydroxy-lower alkylamine, for example mono-, di- or tri-ethanolamine. In addition, corresponding internal salts may also be formed. As a particular subset within the scope of the invention there may be mentioned agrochemically advantageous salts. In view of the close relationship between the compounds of formula (I) in free form and in the form of their salts, any reference hereinbefore or hereinafter to the free compounds of formula (I) or to their respective salts is to be understood as including also the corresponding salts or the free compounds of formula (I), where appropriate and expedient. The same applies in the case of tautomers of compounds of formula (I) and the salts thereof. In each case, the free form is particularly suitable.

Specific compounds of the formula (I) are those wherein

A is a pyrid-3-yl, 2-chloropyrid-5-yl, 2-chloro-1-oxido-5-pyridinio or 2-chlorothiazol-5-yl group; particularly a 2-chloropyrid-5-yl group or a 2-chlorothiazol-5-yl group; wherein Y is —N(R)(R$_2$);

R is C$_1$-C$_6$alkyl, phenyl-C$_1$-C$_4$alkyl, C$_3$-C$_4$alkenyl or C$_3$-C$_4$alkynyl; more especially C$_1$-C$_4$alkyl, such as methyl;

R$_1$ and R$_2$ are independently of each other C$_1$-C$_4$-alkyl or benzyl, or together a group —CH$_2$—CH$_2$—, —CH$_2$—CH$_2$—CH$_2$—, —CH$_2$—O—CH$_2$—, —CH$_2$—S—CH$_2$—, —CH$_2$—NH—CH$_2$—, —CH$_2$—N(CH$_3$)—CH$_2$—, especially —CH$_2$—CH$_2$— or —CH$_2$—O—CH$_2$—, particulary —CH$_2$——O—CH$_2$—; and X is N—NO$_2$ or N—CN, more especially N—NO$_2$.

Specific examples of suitable neonicotinoids within the scope of the invention include thiamethoxam of the formula

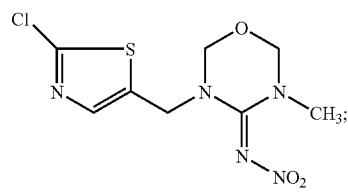

imidacloprid of the formula

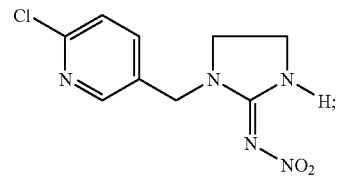

thiacloprid of the formula

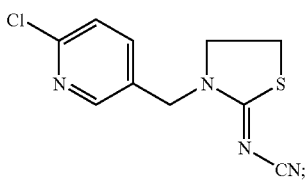

Clothianidin of the formula

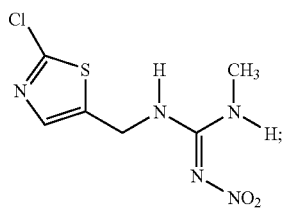

Nitenpyram of the formula

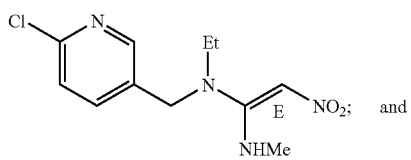

acetamiprid of the formula

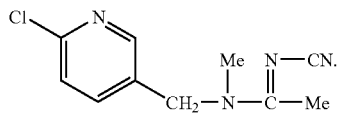

The neonicotinoid compounds are employed in an insecticidally or acaricidally effective amount in the composition.

Mixtures of one or more of the foregoing active compounds also are usable as an active component in the practice of the present invention.

In one embodiment, the insecticidally or acaricidally active compound or compound mixture is present in the composition in an amount of from about 0.5% to about 50% by weight, more particularly from 2 to about 20% w/w.

The term "fungicide" as utilized herein is intended to cover compounds active against phytopathogenic fungi that may belong to a very wide range of compound classes. Examples of compound classes to which the suitable fungicidally active compound may belong include both room temperature (25° C.) solid and room temperature liquid fungicides such as: triazole derivatives, strobilurins, carbamates (including thio- and dithiocarbamates), benzimidazoles(thiabendazole), N-trihalomethylthio compounds (captan), substituted benzenes, carboxamides, phenylamides and phenylpyrroles, and mixtures thereof.

Examples of suitable individual compounds of the above mentioned compound classes are listed below. Where known, the common name is used to designate the individual compounds (q.v. the Pesticide Manual, 12th edition, 2001, British Crop Protection Council).

Suitable triazole derivatives include propiconazole, difenconazole, tebuconazole, tetraconazole and triticonazole.

Suitable strobilurins include trifloxystrobin, azoxystrobin, kresoxim-methyl and picoxystrobin.

Suitable carbamates include thiram.

Suitable substituted benzenes include PCNB and chlorothalonil.

Suitable carboxamides include carboxin.

Specific phenylamides usable in the compositions and methods falling within the scope of the present invention include metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M).

A specific phenylpyrrole usable in the compositions and methods falling within the scope of the present invention is fludioxonil.

Other suitable fungicidal compounds that may mentioned are Benomyl (also known as Benlate), Bitertanol, Carbendazim, Capropamid, Cymoxanil, Cyprodinil, Ethirimol, Fenpiclonil, Fenpropimorph, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Pefurazoate, Pencycuron, Prochloraz, Propamocarb hydrochloride, Pyroquilon, Silthiopham—see MON 65500, Tecnazene, Thifluzamide, Thiophenate-methyl, Tolclofos-methyl, Triadimenol, Triazoxide and Triflumizole.

The fungicidally active compounds are employed in a fungicidally effective amount in the composition.

Mixtures of one or more of the foregoing fungicidally active compounds also are usable as an active component in the practice of the present invention.

In one embodiment, mixtures of at least one ambient liquid fungicide (for example, a phenylamide such as R-metalaxyl) and at least one ambient solid fungicide (for example, a phenylpyrrole such as fludioxonil) are employed.

In one embodiment, the fungicidally active compound or compound mixture is present in the composition in an amount of from about 0.5% to about 50% by weight, more specifically, from 2 to about 20% by weight of the entire composition.

Surface Active Agent

The aqueous compositions contain at least about 2% up to about 10% by weight of a surface-active agent (a). In one embodiment, the aqueous compositions contain from 3% up to 7% by weight of a surface-active agent (a).

The surface active agent (a) comprises (a1) at least one anionic surfactant. In general, the anionic surfactant may be any known in the art. Suitable anionic surfactants are in general oligomers and polymers, as well as polycondensates, which contain a sufficient number of anionic groups to ensure their water-solubility. Suitable anionic surfactants include alcohol sulfates, alcohol ether sulfates, alkylaryl ether sulfates, alkylaryl sulfonates such as alkylbenzene sulfonates and alkylnaphthalene sulfonates and salts thereof, alkyl sulfonates, mono- or di-phosphate esters of polyalkoxylated alkyl alcohols or alkylphenols, mono- or disulfosuccinate esters of $C_{12}$-$C_{15}$ alkanols or polyalkoxylated $C_{12}$-$C_{15}$ alkanols, alcohol ether carboxylates, phenolic ether carboxylates, polybasic acid esters of ethoxylated polyoxyalkylene glycols consisting of oxybutylene or the residue of tetrahydrofuran, sulfoalkylamides and salts thereof such as N-methyl-N-oleoyltaurate Na salt, polyoxyalkylene alkylphenol carboxylates, polyoxyalkylene alcohol carboxylates alkyl polyglycoside/alkenyl succinic anhydride condensation products, alkyl ester sulfates, napthalene sulfonates, naphthalene formaldehyde condensates, alkyl sulfonamides, sulfonated aliphatic polyesters, sulfate esters of styrylphenyl alkoxylates, and sulfonate esters of styrylphenyl alkoxylates and their corresponding sodium, potassium, calcium, magnesium, zinc, ammonium, alkylammonium, diethanolammonium, or triethanolammonium salts, salts of ligninsulfonic acid such as the sodium, potassium, magnesium, calcium or ammonium salt, polyarylphenol polyalkoxyether sulfates and polyarylphenol polyalkoxyether phosphates, and sulfated alkyl phenol ethoxylates and phosphated alkyl phenol ethoxylates.

Specific examples of suitable anionic surfactants include: Geropon T77 (Rhodia) (N-methyl-N-oleoyltaurate Na salt); Soprophor 4D384 (Rhodia) (tristyrylphenol sulphate); Reax 825 (Westvaco) (ethoxylated lignin sulfonate); Stepfac 8171 (Stepan) (ethoxylated nonylphenol phosphate ester); Ninate 401-A (Stepan) (calcium alkylbenzene sulfonate); Emphos CS-131 (Witco) (ethoxylated nonylphenol phosphate ester); Atphos 3226 (Uniquema) (ethoxylated tridecylalcohol phosphate ester). Suitable anionic surfactants can be prepared by methods known per se and also are commercially available.

The surface-active agent comprising a1) at least one anionic surfactant may optionally further comprise a2) one or more nonionic surfactants. As used herein, "nonionic surfactants" are different compounds from the water-dispersible and water-soluble polymers b) described herein.

Exemplary nonionic surfactants include polyarylphenol polyethoxy ethers, polyalkylphenol polyethoxy ethers, polyglycol ether derivatives of saturated fatty acids, polyglycol ether derivatives of unsaturated fatty acids, polyglycol ether derivatives of aliphatic alcohols, polyglycol ether derivatives of cycloaliphatic alcohols, fatty acid esters of polyoxyethylene sorbitan, alkoxylated vegetable oils, alkoxylated acetylenic diols, polyalkoxylated alkylphenols, fatty acid alkoxylates, sorbitan alkoxylates, sorbitol esters, $C_8$-$C_{22}$ alkyl or alkenyl polyglycosides, polyalkoxy styrylaryl ethers, alkylamine oxides, block copolymer ethers, polyalkoxylated fatty glyceride, polyalkylene glycol ethers, linear aliphatic or aromatic polyesters, organo silicones, polyaryl phenols, sorbitol ester alkoxylates, and mono- and diesters of ethylene glycol and mixtures thereof.

Specific examples of suitable nonionic sufactants include: Genapol X-060 (Clariant) (ethoxylated fatty alcohol); Sorpohor BSU (Rhodia) (ethoxylated tristyrylphenol); Makon TD-6 (Stepan) (ethoxylated fatty alcohol); BRIJ 30 (Uniquema) (ethoxylated lauryl alcohol); Witconol CO-360 (Witco) (ethoxylated castor oil); Witconol NP-60 (Witco) (ethoxylated nonylphenol). Suitable nonionic surfactants can be prepared by methods known per se and also are commercially available.

In addition to anionic and nonionic surfactants, certain cationic or zwitterionic surfactants a3) also are suitable for use in the present invention such as alkanol amides of $C_8$-$C_{18}$ fatty acids and $C_8$-$C_{18}$ fatty amine polyalkoxylates, $C_{10}$-$C_{18}$ alkyldimethylbenzylammonium chlorides, coconut alkyldimethylaminoacetic acids, and phosphate esters of $C_{8-18}$ fatty amine polyalkoxylates.

Carrier

The aqueous composition also comprises (b), at least about 4 and up to about 20%, more specifically from 5 to about 15% of at least one inorganic solid carrier.

The inorganic solid carrier is a natural or synthetic solid material that is insoluble in water. This carrier is generally inert and acceptable in agriculture, especially on the treated seed or other propagation material. It can be chosen, for example, from clay, natural or synthetic silicates, titanium dioxide, magnesium silicate, aluminum silicate, talc, pyrophyllite clay, silica, attapulgite clay, kieselguhr, chalk, diatomaceous earth, lime, calcium carbonate, bentonite clay, Fuller's earth, and the like such as described in the CFR 180.1001. (c) & (d).

Antifreeze

The aqueous composition also comprises (c), at least about 3 and up to about 25% of at least one antifreeze agent, more specifically from 6 to about 20% by weight.

Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like.

As a particular subset of suitable antifreeze materials there can be mentioned ethylene glycol, propylene glycol and glycerin.

Additional Components

The aqueous composition optionally includes (d) at least one polymer selected from water-soluble and water-dispersible film-forming polymers. Suitable polymers have an average molecular weight of at least about 1,000 up to about 100,000; more specifically at least about 5,000, up to about 100,000. The aqueous compositions generally contain from about 0% to about 10% by weight of the composition of polymer (d). In a specific embodiment, the compositions contain from about 1.0% upto about 5% by weight of a film-forming polymer (d).

Suitable polymers are selected from d1) alkyleneoxide random and block copolymers such as ethylene oxide-propylene oxide block copolymers (EO/PO block copolymers) including both EO-PO-EO and PO-EO-PO block copolymers;

ethylene oxide-butylene oxide random and block copolymers, $C_{2-6}$ alkyl adducts of ethylene oxide-propylene oxide random and block copolymers, $C_{2-6}$ alkyl adducts of ethylene oxide-butylene oxide random and block copolymers, d2) polyoxyethylene-polyoxypropylene monoalkylethers such as methyl ether, ethyl ether, propyl ether, butyl ether or mixtures thereof.

d3) vinylacetate/vinylpyrrolidone copolymers, d4) alkylated vinylpyrrolidone copolymers, d5) polyvinylpyrrolidone, and d6) polyalkyleneglycol including the polypropylene glycols and polyethylene glycols.

Specific examples of suitable polymers include Pluronic P103 (BASF) (EO-PO-EO block copolymer), Pluronic P65 (BASF) (EO-PO-EO block copolymer), Pluronic P108 (BASF) (EO-PO-EO block copolymer), Vinamul 18160 (National Starch) (polyvinylacetate), Agrimer 30 (ISP) (polyvinylpyrrolidone), Agrimer VA7w (ISP) (vinyl acetate/vinylpyrrolidone copolymer), Agrimer AL 10 (ISP) (alkylated vinylpyrrolidone copolymer), PEG 400 (Uniqema) (polyethylene glycol), Pluronic R 25R2 (BASF) (PO-EO-PO block copolymer), Pluronic R 31R1 (BASF) (PO-EO-PO block copolymer) and Witconol NS 500LQ (Witco) (butanol PO-EO copolymer).

The composition also optionally contains (e) at least one thickener.

In one embodiment, the thickener is present in the aqueous composition in an amount from about 0.01% to about 25% w/w, more specifically from 0.02 to 10% by weight.

Illustrative of thickeners (water-soluble polymers which exhibit pseudoplastic properties in an aqueous medium) are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, alkali metal salts of poly(meth)acrylate, and the like.

As suitable thickeners there may also be mentioned attapulgite-type clay, carrageenan, croscarmellose sodium, furcelleran, glycerol, hydroxypropyl methylcellulose, polystyrene, hydroxypropyl cellulose, hydroxypropyl guar gum, and sodium carboxymethylcellulose. Xanthan gum is preferred.

The aqueous composition according to the invention can be employed together with the adjuvants customary in formulation technology, biocides, biostats, emulsifiers (lethicin, sorbitan, and the like), antifoam agents or application-promoting adjuvants customarily employed in the art of formulation. In addition, there may be mentioned inoculants and brighteners.

Additionally, a coloring agent, such as a dye or pigment is included in the seed coating so that an observer can immediately determine that the seeds are treated. The dye is also useful to indicate to the user the degree of uniformity of the coating applied.

The inventive compositions contain and/or may be applied together or sequentially with further active compounds. These further compounds can be fertilizers or micronutrient donors or other preparations that influence plant growth. They can also be selective herbicides, fungicides, other insecticides, bactericides, insect growth regulators, plant growth regulators, nematicides, molluscicides or mixtures of several of these preparations.

Process

The aqueous neonicotinoid compositions of the invention can be prepared by processes known in the art.

In one embodiment, the aqueous neonicotinoid compositions of the invention can be prepared by a process which comprises the steps: (a) forming a premix with at least one solid active compound and at least one surfactant; (b) forming a premix of a carrier and water, and (c) sequentially adding the premixes (a) and (b) and the remaining ingredients to water while stirring to form as evenly dispersed composition.

In one aspect, the solid active compounds may be wet milled prior to being added to the mixture (c).

The final composition can be screened if desired to remove any insoluble particles.

Aqueous Composition

Insecticidal compositions in accordance with the invention may take the form of aqueous solutions, dispersions, suspensions, emulsions or suspoemulsions. In one embodiment, the composition is a ready for use suspension or suspoemulsion.

The average size of the suspended particles is 0.1 to 20, specifically 1.5 to 5 microns when measured with a laser particle analyzer, e.g a CILAS 920 apparatus.

The viscosity of the aqueous composition is 50 to 2000, more specifically 100 to 1000 mPas when measured with a BROOKFIELD viscometer with spindle 3 at 30 rpm and 25° C.

The aqueous compositions according to the invention are stable and maintain their viscosity and homogeneity for at least 12 months at 25° C.

Use

For the purposes of this invention, seed treatments are defined as chemical or biological substances that are applied to seeds or vegetative plant propagation materials to control disease organisms, insects, or other pests. The seed treatment composition of the invention includes neonicotinoid insecticides/acaricides, but can also include other pesticides such as bactericides and other classes of insecticides. Most seed treatments are applied to true seeds, which have a seed coat surrounding an embryo. However, some seed treatments can be applied to vegetative plant propagation materials such as rhizomes, bulbs, corms or tubers.

The aqueous insecticidal/acaricidal compositions of the invention are formulated for protecting cultivated plants and their propagation materials. The inventive compositions are advantageously formulated for seed treatment applications against soil inhabiting insects, which can damage the crop in the early stages of plant development. For example, the compositions can be formulated to target insects and representatives of the order Acarnia including:

from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Coleoptera, for example,

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scara-*

*beidae, Sitophilus* spp., *Sitotroga* spp., *Tenebrio* spp., *Tribolium* spp. and *Trogoderma* spp.;

from the order Orthoptera, for example,

*Blatta* spp., *Blattella* spp., *Gryllotalpa* spp., *Leucophaea maderae, Locusta* spp., *Periplaneta* spp. and *Schistocerca* spp.;

from the order Isoptera, for example,

*Reticulitermes* spp.;

from the order Psocoptera, for example,

*Liposcelis* spp.;

from the order Anoplura, for example,

*Haematopinus* spp., *Linognathus* spp., *Pediculus* spp., *Pemphigus* spp. and *Phylloxera* spp.;

from the order Mallophaga, for example,

*Damalinea* spp. and *Trichodectes* spp.;

from the order Thysanoptera, for example,

*Frankliniella* spp., *Hercinothrips* spp., *Taeniothrips* spp., *Thrips palmi, Thrips tabaci* and *Scirtothrips aurantii;* from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order Homoptera, for example,

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example,

*Acromyrmex, Afta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Diptera, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella trit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Siphonaptera, for example, *Ceratophyllus* spp. und *Xenopsylla cheopis* and from the order Thysanura, for example, *Lepisma saccharina*; and crucifer flea beetles (*Phyllotreta* spp.), root maggots (*Delia* spp.), cabbage seedpod weevil (*Ceutorhynchus* spp.) and aphids.

Optionally, in addition to the control of insect pests, the aqueous insecticidal compositions of the invention advantageously are formulated with fungicides for seed treatment applications against diseases in the soil, which mostly occur in the early stages of plant development. For example, the compositions can be formulated to target pathogens including Pythium, Tilletia, Gerlachia, Septoria, Ustilago, Fusarium, Rhizoctonia (so-called "damping off complex"); Oomycetes such as Phytophthora, Plasmopara, Pseuderonospora, Bremia etc. as well as against the Botrytis species, Pyrenophora, Monilinia and further representatives of the Ascomycetes, Deuteromycetes and Basidiomycetes classes.

Suitable target crops are especially potatoes, cereals, (wheat, barley, rye, oats, rice), maize, sugar beet, cotton, millet varieties such as sorghum, sun flowers, beans, peas, oil plants such as rape, canola, soybeans, cabbages, tomatoes, eggplants (aubergines), pepper and other vegetables and spices as well as ornamental shrubs and flowers.

Suitable target crops also include transgenic crop plants of the foregoing varieties. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The inventive compositions are particularly suited for dressing applications on plant propagation material. The latter term embraces seeds of all kinds (fruit, tubers, grains), cuttings, cut shoots and the like. The preferred field of application is the treatment of all kinds of seeds (as specified in the target crops above), and in particular the seed treatment of canola, maize, cereals, soybeans and other legumes and crops that are susceptible.

The techniques of seed treatment application are well known to those skilled in the art, and they may be used readily in the context of the present invention. The aqueous neonicotinoid composition of the invention is applied to the seed as slurry or a soak. There also may be mentioned, e.g., film coating or encapsulation. The coating processes are well known in the art, and employ, for seeds, the techniques of film coating or encapsulation, or for the other multiplication products, the techniques of immersion. Needless to say, the method of application of the inventive compositions to the seed may be varied and the invention is intended to include any technique that is to be used.

A preferred method of applying the aqueous insecticidal composition according to the invention consists in spraying or wetting the plant propagation material with the aqueous liquid preparation, or mixing the plant material with such liquid preparation. Also, before the application, the composition of the invention may be diluted with water by simple mixing at ambient temperature in order to prepare an on-farm seed treatment formulation.

The formulation may be applied at application volumes ranging from 200 ml to 3 liters per 100 kg seed, more specifically, from 400 ml to 2 liters per 100 kg seed.

As noted above, the compositions of this invention may be formulated or mixed in the seed treater tank or combined on the seed by overcoating with other seed treating agents. The agents to be mixed with the compounds of this invention may be for the control of pests, nutrition, and the control of plant diseases.

The inventive aqueous insecticidal composition has particular application to concurrent (such as by slurry) and sequential seed treatments.

The aqueous compositions of the invention are both cold and heat stable and can be applied to seeds at temperatures ranging from −20 to 40° C.

Seeds treated with the aqueous composition of the invention have a drying time ranging from 20 to 60 seconds when being treated at room temperature.

The aqueous neonicotinoid compositions of the invention typically are distributed in a storage and shipping system comprising a container ranging in capacity from about 0.1 liter to about 2000 liters.

For example, the aqueous neonicotinoid compositions of the invention can be distributed in small containers, ranging in capacity from about 0.1 liter to about 10 liters, including the standard 2.5 gallon (9.46 liter) containers widely used in the United States, which typically take the form of jugs or flasks with a replaceable screw-cap. They are generally designed for single use and are typically not returned to the supplier when empty, instead being disposed of by the end user in accordance with local agricultural chemical container disposal guidelines, procedures, regulations or laws. Commonly, a plurality of these small containers are packaged within a single box and a plurality of such boxes are shipped on a pallet. During shipment, the small containers (usually within boxes on pallets) can be disposed in an enclosed volume such as provided by a rail boxcar or road truck, the hold of a ship or aircraft, or a modular box container adapted for transport by road, rail and water.

Larger single-use containers, ranging in capacity up to about 200 liters, for example about 50 to about 200 liters, are commonly in the form of drums, and can be shipped in an enclosed volume as described above, one or more per pallet or unpalleted.

The aqueous neonicotinoid compositions of the invention also can be distributed in a large refillable container sometimes known as a bulk or minibulk tank, which typically has an integral pump or connector for an external pump to permit transfer of liquid. Bulk or minibulk tanks having a capacity of about 200 to about 2000 liters or more are typically returned to the supplier when empty and are commonly shipped on a pallet.

A principal feature of the inventive composition is that it provides a treated seed with increased adherence which results in decreased dustiness and the subsequent elimination of related dust problems. Elimination of the dust associated with many seed treatments also eliminates the associated health hazards to those who work with treated seeds, such as processing plant employees, truck drivers, warehouse workers, and farmers.

Still another advantage of this invention is the uniform coating of seeds with non-dusting seed treatment which will not interfere with germination and sprouting of the seed but which will protect the seed and resultant seedling against soil-borne insects and representatives of the order acarina.

EXAMPLES

In order that those skilled in the art will be better able to practice the invention, the following examples are given by way of illustration and not by way of limitation. In the following examples, as well as elsewhere in the specification and claims, temperatures are in degrees Celsius, the pressure is atmospheric and all parts are by weight, unless otherwise clearly indicated. The registered trademarks and other designations denote the following products:

| Product | Composition | Source |
|---|---|---|
| Surfactants | | |
| Geropon T77 | methyl oleytaurate Na-salt | Rhodia |
| Soprophor 4D384 | ethoxylated Tristyrylphenol sulphates | Rhodia |
| Stepan Agent 1411-80A | 4EO nonylphenol/6EO Tallow amine | Stepan |
| Reax 825 | ethoxylated lignin sulfonate | Westvaco |
| Genapol X-060 | Ethoxylated fatty alcohol | Clariant |
| Polymers | | |
| Agrimer ST | Vinylpyrrolidone/styrene block copolymer | ISP |
| Pluronic P103 | EO-PO-EO block copolymer | BASF |
| Pluronic P65 | EO-PO-EO block copolymer | BASF |
| Pluronic P108 | EO-PO-EO block copolymer | BASF |
| Vinamul 18160 | Polyvinylacetate | National Starch |
| Agrimer 30 | Polyvinylpyrrolidone | ISP |
| Agrimer VA 7w | Vinylacetate/vinylpyrrolidone copolymer | ISP |
| Agrimer AL 10 | Alkylated polyvinylpyrrolidone | ISP |
| PEG 400 | Polyethyleneglycol | Unichema |
| Witconol NS 500LQ | Butanol PO-EO block copolymer | Witco |
| Carriers | | |
| Volcaly 325mesh | Aluminum silicate | American Coloid |
| Auxilaries | | |
| Irgalite Red C2B | Pigment red C2B | Ciba Speciality |
| Antifoam A | Silicon oil | Dow Corning |
| Proxel GXL | Bactericide (1,2-Benzisothiazol-3(2H)-one) | |
| Rhodopol 23 | Xanthan gum | |

Example 1

Surfactants (Soprophor 4D384, Reax 835, Stepan Agent 1411-80A), defoaming agent (Antifoam A) and bactericide (Proxel GXL) are mixed with water until a homogeneous phase is achieved. Subsequently, Colorant (Irgalite Red C2B), Drying agent (TiO2), active ingredients are added and mixed. The resulting mixture is then wet-milled through a so-called bead mill (Dyno, Drais, Premier for instance). The milling parameters are set in such a way that the average particle size of the resulting ground premix is within specifications (usually median partical size between 1.5 um and 4.0 um).

Finally, polymer (Pluronic P103) (if any), antifreeze (Glycerine) and thickening agent (xantham gum) are added and the final product is mixed for at least 15 minutes.

Aqueous compositions of Examples 2-21 are prepared by following the procedures given in example 1. The numbers given in the Examples are concentrations in % weight/weight. All embodiments given below are based on an application volume of 1500 ml per 100 kg of seed. However, the active ingredient concentrations in each of the examples given below can be adjusted to application volumes ranging from 200 ml to 3000 ml per 100 kg of seed.

TABLE I

Combination of Clothianidin with fungicides

| | Example: | | | | |
|---|---|---|---|---|---|
| | 2 | 3 | 4 | 5 | 6 |
| Clothianidin | 10% | 30% | 10% | 30% | 10% |
| Carboxim | 3% | 11% | — | — | — |
| Tebuconazole | — | — | 0.1% | 0.6% | — |
| Thiram | 3% | 16% | — | — | — |
| Glycerine | 10% | 15% | — | — | 5% |
| Propylene Glycole | — | — | 20% | 15% | 10% |
| Sulphated Tristyrylphenol | 2% | — | 2% | — | 4% |
| Phosphated Tristyrylphenol | — | 3% | — | — | — |
| Et. fatty alcohol | — | — | 5% | 4% | — |
| Et. Nopnylphenol | — | — | 0.5% | 2% | 2% |
| Na-lignosulfonate | 4% | — | — | — | 2% |
| TiO2 | 10% | 15% | — | — | 10% |
| Clay | — | 0.05% | — | 0.1% | 0.15% |
| Talc | — | — | 15% | 20% | 5% |
| Pigment | 3% | 4% | 3.5% | — | 2% |
| EO-PO-EO block copolymer | — | — | 1.0% | — | 2% |
| vinyl acetate/ vinylpyrrolidone | — | — | — | 3% | 1% |
| Xantham gum | 0.2% | 0.2% | 0.2% | 0.15 | 0.25% |
| Biocide | 0.1% | 0.1% | 0.1% | 0.1% | 0.1% |
| Water | add 100 | add 100 | add 100 | add 100 | add 100 |

TABLE II

Combination of Acetamiprid with fungicides

| | Example: | | | | |
|---|---|---|---|---|---|
| | 7 | 8 | 9 | 10 | 11 |
| Acetamiprid | 10% | 30% | 10% | 30% | 10% |
| Triticonazole | .15% | .45% | — | — | — |
| Iprodione | — | — | 3% | 18% | 3% |
| Metalaxyl | 0.1% | 1.2% | — | 0.1% | 1.2% |
| Glycerine | 15% | 15% | — | — | 5% |
| Propylene Glycole | — | — | 19% | 15% | 10% |
| Sulphated Tristyrylphenol | — | 1% | 2% | — | 4% |
| Phosphated Tristyrylphenol | 4% | 1% | — | — | — |
| Et. fatty alcohol | — | — | — | 4% | — |
| Et. Nonylphenol | — | 2% | 2.5% | 2% | 2% |
| Na-lignosulfonate | 2% | — | — | — | 2% |
| TiO2 | 10% | 15% | — | — | 10% |
| Clay | 0.2% | 0.1% | — | — | 0.26% |
| Talc | — | — | 15% | 20% | 5% |
| Pigment | 3% | 4% | 3.5% | — | 2% |
| EO-PO-EO block copolymer | — | — | 1.0% | — | 2% |
| vinyl acetate/ vinylpyrrolidone | — | — | — | 3% | 1% |
| Xantham gum | 0.2% | 0.2% | 0.2% | 0.15 | 0.25% |
| Biocide | 0.1% | 0.1% | 0.1% | 0.1% | 0.1% |
| Water | add 100 | add 100 | add 100 | add 100 | add 100 |

TABLE III

Combination of Imidacloprid with fungicides

| | Example: | | | | |
|---|---|---|---|---|---|
| | 12 | 13 | 14 | 15 | 16 |
| Imidacloprid | 25% | 45% | 25% | 45% | 25% |
| Tebuconazole | 0.1% | 0.6% | 0.1% | 0.6% | — |
| Metalaxyl | 0.1% | 1.2% | — | — | — |
| Thiram | — | — | 3% | 18% | 18% |
| Glycerine | 15% | 15% | — | — | 5% |
| Propylene Glycole | — | — | 19% | 15% | 10% |
| Sulphated Tristyrylphenol | — | 1% | 2% | — | 4% |
| Phosphated Tristyrylphenol | 4% | 1% | — | — | — |
| Et. fatty alcohol | — | — | — | 4% | — |
| Et. Nonylphenol | — | 2% | 2.5% | 2% | 2% |
| Na-lignosulfonate | 2% | — | — | — | 2% |
| TiO2 | 10% | 15% | — | — | 10% |
| Clay | 0.2% | 0.1% | — | — | 0.26% |
| Talc | — | — | 15% | 20% | 5% |
| Pigment | 3% | 4% | 3.5% | — | 2% |
| EO-PO-EO block copolymer | — | — | 1.0% | — | 2% |
| vinyl acetate/ vinylpyrrolidone | — | — | — | 3% | 1% |
| Xantham gum | 0.2% | 0.2% | 0.2% | 0.15 | 0.25% |
| Biocide | 0.1% | 0.1% | 0.1% | 0.1% | 0.1% |
| Water | add 100 | add 100 | add 100 | add 100 | add 100 |

TABLE IV

Combination of Thiamethoxam with fungicides

| | Example: | | | | |
|---|---|---|---|---|---|
| | 17 | 18 | 19 | 20 | 21 |
| Thiamethoxam | 10% | 25% | 10% | 25% | 10% |
| Fludioxoinil | 0.1% | 0.4% | 0.1% | 0.4% | — |
| Difenoconazole | 0.6% | 1.3% | — | — | — |
| Mefenoxam | 0.4% | 0.8% | 0.4% | 0.8% | 0.4% |
| Myclobutanil | — | — | 0.5% | 2.0% | — |
| Glycerine | 15% | 15% | — | — | 5% |
| Propylene Glycole | — | — | 19% | 15% | 10% |
| Sulphated Tristyrylphenol | — | 1% | 2% | — | 4% |
| Phosphated Tristyrylphenol | 4% | 1% | — | — | — |
| Et. fatty alcohol | — | — | — | 4% | — |
| Et. Nonylphenol | — | 2% | 2.5% | 2% | 2% |
| Na-lignosulfonate | 2% | — | — | — | 2% |
| TiO2 | 10% | 15% | — | — | 10% |
| Clay | 0.2% | 0.1% | — | — | 0.26% |
| Talc | — | — | 15% | 20% | 5% |
| Pigment | 3% | 4% | 3.5% | — | 2% |
| EO-PO-EO block copolymer | — | — | 1.0% | — | 2% |
| vinyl acetate/ vinylpyrrolidone | — | — | — | 3% | 1% |
| Xantham gum | 0.2% | 0.2% | 0.2% | 0.15 | 0.25% |
| Biocide | 0.1% | 0.1% | 0.1% | 0.1% | 0.1% |
| Water | add 100 | add 100 | add 100 | add 100 | add 100 |

Although the foregoing invention has been described in some detail by way of illustration and example for purposes of clarity of understanding, it will be apparent that various changes and modifications may be practiced within the scope of the appended claims.

What is claimed is:

1. An aqueous composition comprising an insecticidally effective amount of thiamethoxam, a fungicidally effective amount of fludioxonil, mefenoxam and azoxystrobin, and a blend of the following components, by weight:
   a) 2-10% of at least one surface active agent selected from tristyrylphenol sulfate, N-methyl-N-oleoyltaurate and salts thereof, phosphate ester of polyalkoxylated alkyl alkylphenol, and lignosulfonic acid and alkoxylated salts thereof;
   b) 4-20% of solid inorganic carrier selected from magnesium silicate and aluminum silicate; and
   c) 3-20% of glycerine.

2. A composition according to claim 1, comprising an insecticidally effective amount of thiamethoxam, a fungicidally effective amount of fludioxonil, mefenoxam and azoxystrobin, and a blend of the following components, by weight:
   a) 2-10% of at least one surface active agent selected from tristyrylphenol sulfate, N-methyl-N-oleoyltaurate and salts thereof, phosphate ester of polyalkoxylated alkyl alkylphenol, and ethoxylated lignosulfonic acid, sodium salt;
   b) 4-20% of magnesium silicate; and
   c) 3-20% of glycerine.

3. Pest-resistant plant propagation material comprising plant propagation material treated with a pesticidally effective amount of a composition according to claim 1.

4. Plant propagation material according to claim 3, wherein said plant propagation material is a plant seed selected from potatoes, wheat, barley, rye, oats, rice, maize, sugar beet, cotton, sorghum, sun flowers, beans, peas, canola, rape, soybeans, cabbages, tomatoes, eggplants and pepper.

5. Plant propagation material according to claim 4, wherein said plant propagation material is a transgenic plant seed.

6. A method of protecting plant propagation material against attack by insects and phytopathogenic fungi which comprises treating said plant propagation material with a pesticidally effective amount of a composition according to claim 1.

7. A method according to claim 6, wherein said plant propagation material is a plant seed selected from potatoes, wheat, barley, rye, oats, rice, maize, sugar beet, cotton, sorghum, sun flowers, beans, peas, canola, rape, soybeans, cabbages, tomatoes, eggplants and pepper.

8. A method according to claim 7, wherein said plant propagation material is a transgenic plant seed.

9. An aqueous composition comprising an insecticidally effective amount of thiamethoxam, a fungicidally effective amount of difenoconazole, flludioxonil and mefenoxam, and a blend of the following components, by weight:
   a) 2-10% of at least one surface active agent selected from phosphate ester of polyalkoxylated alkyl alkylphenol, and lignosulfonic acid and alkoxylated salts thereof;
   b) 4-20% of solid inorganic carrier selected from clay, natural or synthetic silicates, titanium dioxide, and talc;
   c) 3-20% glycerine.

10. The composition according to claim 9, comprising an insecticidally effective amount of thiamethoxam, a fungicidally effective amount of difenoconazole, flludioxonil and mefenoxam, and a blend of the following components, by weight:
    a) 2-10% of at least one surface active agent selected from styrylphenol polyethoxyester phosphate; ethoxylated lignosulfonic acid, sodium salt;
    b) 4-20% of titanium dioxide;
    c) 3-20% glycerine.

11. Pest-resistant plant propagation material comprising plant propagation material treated with a pesticidally effective amount of a composition according to claim 9.

12. Plant propagation material according to claim 11, wherein said plant propagation material is a plant seed selected from potatoes, wheat, barley, rye, oats, rice, maize, sugar beet, cotton, sorghum, sun flowers, beans, peas, canola, rape, soybeans, cabbages, tomatoes, eggplants and pepper.

13. Plant propagation material according to claim 12, wherein said plant propagation material is a transgenic plant seed.

* * * * *

UNITED STATES PATENT AND TRADEMARK OFFICE
CERTIFICATE OF CORRECTION

| | | |
|---|---|---|
| PATENT NO. | : 7,307,043 B2 | Page 1 of 1 |
| APPLICATION NO. | : 10/919626 | |
| DATED | : December 11, 2007 | |
| INVENTOR(S) | : Christian Schlatter and Ravi Ramachandran | |

It is certified that error appears in the above-identified patent and that said Letters Patent is hereby corrected as shown below:

Column 18, lines 10 and 20, the term "flludioxonil" should read --fludioxonil--; line 16, the word --and-- should follow the term "talc;"; line 26, the word --and-- should follow the term "dioxide;"

Signed and Sealed this

Twenty Second Day of April, 2008

JON W. DUDAS
*Director of the United States Patent and Trademark Office*